US00PP30140P3

(12) United States Plant Patent
Brown

(10) Patent No.: US PP30,140 P3
(45) Date of Patent: Jan. 29, 2019

(54) LANDSCAPE SHRUB ROSE PLANT NAMED 'RADGARDEBWHITE'

(50) Latin Name: *Rosa hybrida*
Varietal Denomination: Radgardebwhite

(71) Applicant: The Conard-Pyle Company, West Grove, PA (US)

(72) Inventor: Jason Brown, Elkton, MD (US)

(73) Assignee: The Conrad-Pyle Company, West Grove, PA (US)

( * ) Notice: Subject to any disclaimer, the term of this patent is extended or adjusted under 35 U.S.C. 154(b) by 0 days.

(21) Appl. No.: 15/731,527

(22) Filed: Jun. 22, 2017

(65) Prior Publication Data

US 2018/0376636 P1 Dec. 27, 2018

(51) Int. Cl.
*A01H 5/02* (2018.01)
*A01H 6/74* (2018.01)

(52) U.S. Cl.
USPC ..... Plt./103
CPC ..... *A01H 6/749* (2018.05); *A01H 5/02* (2013.01)

(58) Field of Classification Search
USPC ..... Plt./103
CPC ..... A01H 5/0222
See application file for complete search history.

(56) References Cited

U.S. PATENT DOCUMENTS

PP20,273 P2 9/2009 Radler
PP22,172 P2 10/2011 Radler

*Primary Examiner* — Kent L Bell
(74) *Attorney, Agent, or Firm* — Buchanan Ingersoll & Rooney PC

(57) ABSTRACT

A new and distinct variety of landscape shrub rose plant herein referred to by its cultivar name, 'Radgardebwhite', is provided which forms in abundance on a substantially continuous basis attractive, double white colored blossoms. The vegetation is vigorous and the growth habit is very bushy and rounded. Attractive, semi-glossy, medium green foliage is formed. Excellent disease resistance is exhibited. Additionally, the new variety is particularly well suited for growing as distinctive ornamentation in the landscape.

1 Drawing Sheet

Botanical/commercial classification: The new plant variety described herein is a landscape shrub rose within the botanical classification *Rosa* hybrid. The new landscape shrub rose is of the variety denominated 'Radgardebwhite'.

SUMMARY OF THE INVENTION

The new and distinct variety of *Rosa hybrida* landscape shrub rose plant was discovered as a naturally occurring branch mutation of the variety 'Radcarn' (U.S. Plant Pat. No. 22,172) in West Grove, Pa., U.S.A. in June 2006.

It was found that the new variety of landscape shrub rose plant of the present invention possesses the following combination of characteristics:

(a) abundantly and substantially continuously forms attractive, double white colored blossoms,
(b) exhibits a very bushy and rounded growth habit,
(c) forms vigorous vegetation,
(d) forms attractive ornamental semi-glossy, medium green foliage, and
(e) exhibits excellent resistance.

The new variety well meets the needs of the horticultural industry and can be grown to advantage in the landscape, including parks, gardens, public areas, and residential landscapes, where attractive ornamentation is to be provided.

The new variety can be readily distinguished from its ancestors. More specifically, the 'Radcarn' variety (i.e., the parent variety) displays dissimilar double bicolored pink and white flowers. Additionally, the new variety can be readily distinguished from other shrub roses. For example, the 'Radwhite' variety (U.S. Plant Pat. No. 20,273) has fewer petals than the new variety.

The new variety has been found to undergo asexual propagation in Wasco, Calif. by a number of routes, such as vegetative cuttings. Asexual propagation has shown that the characteristics of the new variety are homogeneous and stable and are strictly transmissible by asexual propagation from one generation to another. Accordingly, the new variety undergoes asexual propagation in a true-to-type manner.

The new variety has been named 'Radgardebwhite'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plant of the new variety was approximately three years of age and was observed during June of 2012 while growing outdoors on its own roots in West Grove, Pa., U.S.A.

FIG. 1—illustrates a specimen of a plant displaying blossoms.

DETAILED BOTANICAL DESCRIPTION

The chart used in the identification of the colors is that of The Royal Horticultural Society ("R.H.S.") (R.H.S. Colour Chart, 2015 Edition). The description is based on the observation of plants during June while growing outdoors as their own roots at West Grove, Pa., U.S.A.

Class: Landscape Shrub Rose.

Plant:

*Growth habit*.—Very bushy, upright, and rounded.

*Vegetation*.—Vigorous.

*Foliage*.—Attractive semi-glossy, medium green.

*Blossoms*.—Attractive, double white colored.

*Height*.—Approximately up to 3 feet on average.

*Width*.—Approximately up to 3 feet on average.

Branches:

*Color*.—Commonly near Yellow-Green Group 146A transitions to near Greyed-Orange Group 177A on old wood and commonly near Yellow-Green Group 146A on young stems.

*Length*.—Main stems are approximately 29.0 cm on average and secondary stems are approximately 15.0 cm on average.

*Diameter*.—Approximately 5.0 mm on average.

*Thorns*.—Young thorns: color is commonly near Greyed-Orange Group 176C, length is approximately 3.0 mm on average, and width at point of attachment is approximately 1.0 mm on average. Old thorns: color is commonly near Greyed-Orange Group 176A, length is approximately 5.0 mm on average, and width at point of attachments is approximately 2.0 mm on average.

Foliage:

*Young foliage*.—Color: upper surface is commonly near Yellow-Green Group 144A and under surface is commonly near Yellow-Green Group 152B.

*Old foliage*.—Color: upper surface is commonly near Yellow-Green Group 147A and under surface is commonly near Yellow-Green Group 147B.

Leaflets:

*Number*.—Commonly 3, 5, and 7.

*Shape*.—Ovate. Apex: acute. Base: cuneate.

*Margin*.—Serrate.

*Texture*.—Upper surface: smooth. Under surface: smooth.

*Size*.—Terminal leaflet: length is approximately 6.0 cm on average and width is approximately 3.0 cm on average. Lower leaflets: length is approximately 4.5 cm on average and width is approximately 2.0 cm on average. 5-leaflet leaf: length is approximately 10.0 cm on average and width is approximately 10.5 cm on average.

Inflorescence:

*Number of flowers*.—Commonly approximately 26 blooms on average on a single plant at once.

*Number of blooms per stem*.—Commonly between 1 and 5 blooms per stem on average.

*Peduncle*.—Color: commonly near Yellow-Green Group 144A. Diameter: approximately 3.0 mm on average. Length: approximately 3.5 cm on average. Surface texture: commonly sparely covered in short, flexible thorns that measure approximately less than 2 mm on average in length.

*Sepals*.—Number: commonly 5. Upper surface: color is commonly near Yellow-Green Group 144A and is covered in short pubescence. Under surface: color is commonly near Yellow-Green Group 144B and texture is puberulent. Size: length is approximately 1.6 cm on average and width is approximately 7.0 mm on average. Shape: lanceolate overall with a truncate base where it fuses to the receptacle. Apex: acute. Margin: entire with occasional extensions on two or three sepals measuring approximately 2.0 mm in length on average and approximately 1.0 mm in width on average.

*Bud*.—Shape: ovoid. Size: approximately 2.0 cm on average in length and approximately 1.5 cm on average in width. Color (when opening): commonly near Yellow Group 4C.

*Flower*.—Form: double, cuplike. Diameter: approximately 3.0 cm on average. Depth: approximately 2.0 cm on average. Color: upper and under surfaces are commonly near White Group N155B. Fragrance: very light sweet fragrance. Number of petals: approximately 16 on average. Petal drop: good. Petal size: length is approximately 2.7 cm on average and width is approximately 2.2 cm on average. Petal shape: overall broadly obovate with a round apex and cuneate base. Petal margin: entire. Stamen: number is approximately 135 on average. Anthers: number is approximately 135 on average and color is commonly near Greyed-Yellow Group 162B. Filaments: length is approximately 3.0 mm on average and color is commonly near Greyed-Yellow Group 160B. Pistils: arrangement is separate and free, number is approximately 50 on average. Style: color is commonly near Greyed-Yellow Group 160A and length is approximately 1.0 cm on average. Stigma: color is commonly near Greyed-Yellow Group 160A and diameter is commonly less than 1.0 mm on average.

*Receptacle*.—Achenes: stand on the bottom and wall. Size: approximately 1.0 cm in diameter. Shape: round. Color: commonly near Yellow-Green Group 144A. Surface texture: smooth.

Development:

*Vegetation*.—Medium green, vigorous, and strong.

*Blooming*.—Abundant and substantially continuous from spring through frost.

*Resistance to diseases*.—Excellent, especially for black spot, rust, and mildews.

The new 'Radgardebwhite' variety has not been observed under all possible environmental conditions to date. Accordingly, it is possible that the phenotypic expression may vary somewhat with changes in light intensity and duration, cultural practices, and other environmental conditions.

I claim:

1. A new and distinct landscape shrub rose plant characterized by the following combination of characteristics:

(a) abundantly and substantially continuously forms attractive, double white colored blossoms, (b) exhibits a very bushy and rounded growth habit, (c) forms vigorous vegetation, (d) forms attractive ornamental semi-glossy, medium green foliage, and (e) exhibits excellent resistance;

substantially as herein shown and described.

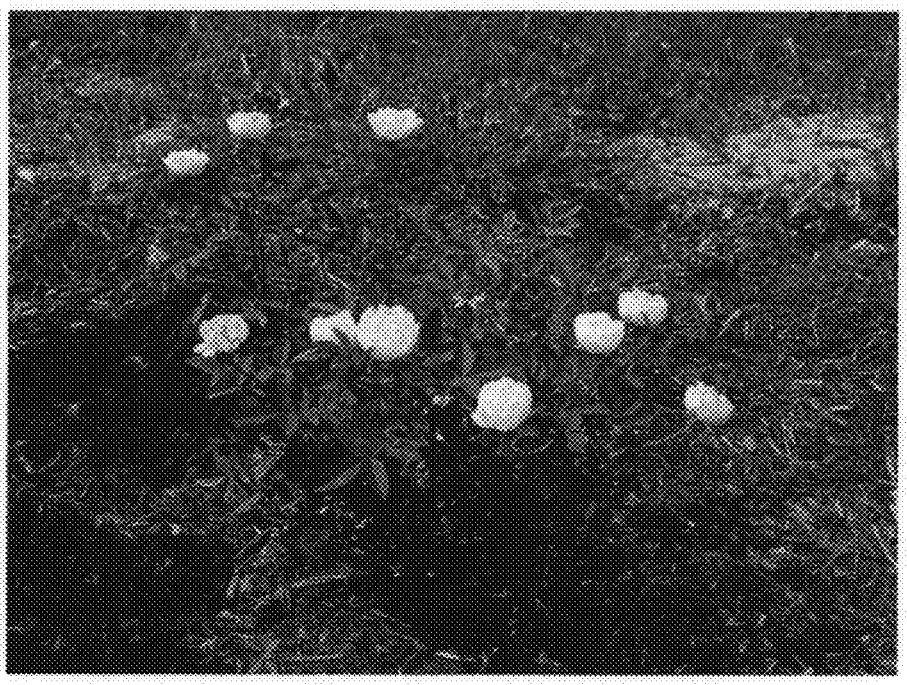

* * * * *